US008232046B2

(12) United States Patent
Chalumeau et al.

(10) Patent No.: US 8,232,046 B2
(45) Date of Patent: Jul. 31, 2012

(54) DISTINCTION BETWEEN BACTERIAL MENINGITIS AND VIRAL MENINGITIS

(75) Inventors: Martin Chalumeau, Paris (FR); Francois Dubos, Lille (FR); Dominique Gendrel, Paris (FR); Gerard L. Breart, Saint-Cloud (FR)

(73) Assignee: Assistance Publique-Hopitaux de Paris, Paris (FR)

( * ) Notice: Subject to any disclaimer, the term of this patent is extended or adjusted under 35 U.S.C. 154(b) by 591 days.

(21) Appl. No.: 12/097,711

(22) PCT Filed: Dec. 14, 2006

(86) PCT No.: PCT/FR2006/002734
§ 371 (c)(1),
(2), (4) Date: Jan. 5, 2009

(87) PCT Pub. No.: WO2007/068830
PCT Pub. Date: Jun. 21, 2007

(65) Prior Publication Data
US 2009/0221021 A1 Sep. 3, 2009

(30) Foreign Application Priority Data
Dec. 14, 2005 (FR) ..................................... 05 12687

(51) Int. Cl.
*C12Q 1/00* (2006.01)
*G01N 31/00* (2006.01)
*G01N 33/48* (2006.01)
(52) U.S. Cl. .................... 435/4; 436/8; 436/15; 436/16; 436/63
(58) Field of Classification Search .......... 435/4; 436/8, 436/15, 16, 63
See application file for complete search history.

(56) References Cited

U.S. PATENT DOCUMENTS

| 5,330,909 | A | 7/1994 | Yamashita et al. |
| 6,133,427 | A | 10/2000 | Yamashita et al. |
| 6,451,311 | B2 | 9/2002 | Althaus et al. |
| 6,905,687 | B2 | 6/2005 | Althaus et al. |

FOREIGN PATENT DOCUMENTS

| FR | 0512687 | 12/2005 |
| WO | 9720231 A1 | 6/1997 |
| WO | WO2007068830 | 6/2007 |

OTHER PUBLICATIONS

Jereb, M. et al. Infection, vol. 29, No. 4, pp. 209-212, 2001.*
PCT International Search Report; Apr. 3, 2007.
Bender Andreas et al.; "Severe symptomatic aseptic chemical meningitis following myelography—The role of procalcitonin"; Neurology, vol. 63, No. 7, Oct. 2004, pp. 1311-1313, XP002379561 ISSN: 0028-3878.
Ferriere F; "Procalcitonin; A new marker for bacterial infections" Annales De Biologie Clinique, vol. 58, No. 1, Jan. 2000, pp. 49-59, XP002379558 ISSN: 0003-3898.
Gendrel D; "Apport des donnees biochimiques dans le diagnostic des meningites purulentes communautaires" Medecine Et Maladies Infectieuses, Societe Francaise D'Editions Medicales, Paris, FR, vol. 26, Dec. 1996, pp. 1068-1072, XP004907301 ISSN: 0399-077X.
Gendrel et al.; "Infection urinaire et marqueurs biologiques: proteine C reactive, interleukines et procalcitonine" Archives De Pediartie, Elsevier, Paris, FR, vol. 5, 1998, pp. 269S-273S, XP005033143 ISSN: 0929-693X.
Jereb M et al.; "Predictive value of serum and cerebrospinal fluid procalcitonin levels for the diagnosis of bacterial meningitis" Infection, vol. 29, No. 4, Aug. 2001, pp. 209-212, XP002379559 ISSN: 0300-8126.
Mary R et al.; "[Acuta meningitidis, acute phase proteins and procalcitontin.]" Annuales De Biologie Clinique, vol. 61, No. 2, 2003, pages 127-137, XP002379560 ISSN: 0003-3898.
Van Rossum A et al.; "Procalcitonin as an early marker of infection in neonates and children" Lancet Infectious Deseases, US, vol. 4, No. 10, Oct. 2004, pp. 620-630, XP004808552 ISSN: 1473-3099.
Baker, et al., "Failure of Infant Observation Scales in Detecting Serious Illness in Febrile, 4-to 8-Week-Old Infants," Pediatrics, 1990, pp. 1040-1043, vol. 85.
Baraff, et al., "Practive Guideline for the Management of Infants and Children 0 to 36 Months of Age With Fever Without Source," Pediatrics, 1993, pp. 1-12, vol. 2.
Bonsu, et al., "Differentiating Acute Bacterial Meningitis from Acute Viral Meningitis Among Children With Cerebrospinal Fluid Pleocytosis: A Multivariable Regression Model," The Pediatric Infectious Disease Journal, 2004, pp. 511-517, vol. 23.
Dumonceaux, et al., "Impact of Immunization Against Haemophilus Influenzae on the Incidence of Invasive Infections from Haemophilus Influenzae Infections in the Nord-Pas-de-Calais Area," Archives de Pédiatrie, 1999, 617-624, vol. 6. (Includes English abstract).
Freedman, et al., "Predictors of Bacterial Meningitis in the Era After Haemophilus Influenzae,"Archives of Pediatrics & Adolescent Medicine, 2001, pp. 1301-1306, vol. 155.
Greenlee. "Approach to Diagnosis of Meningitis. Cerebrospinal Fluid Evaluation," Infectious Diseases of North America, 1990, pp. 583-598, vol. 4.
Ghillani, et al., "Identification and Measurement of Calcitonin Precursors in Serum of Patients with Malignant Diseases," Cancer Research, 1989, pp. 6845-6851, vol. 49.
Jaeger, et al., "Validation of a Diagnosis Model for Differentiating Bacterial from Viral Meningitis in Infants and Children under 3.5 Yeasrs of Age," European Journal of Clinical Microbiology & Infectious Diseases, 2000, pp. 418-421, vol. 19.

(Continued)

*Primary Examiner* — Rodney P. Swartz
(74) *Attorney, Agent, or Firm* — Blank Rome LLP

(57) ABSTRACT

The present invention relates to the field of the distinction between bacterial meningitis and viral meningitis. It relates in particular to an in vitro method for detecting the presence of bacterial meningitis, which comprises determining the concentration of procalcitonin present in a test blood sample and of proteins present in a test cerebrospinal fluid sample, and comparing the concentrations thus determined to the concentration of procalcitonin and of proteins present in a reference sample or to a reference value. It also relates to a kit comprising means for detecting procalcitonin and proteins in the cerebrospinal fluid, and to the use thereof for the production of a diagnostic tool for bacterial meningitis.

13 Claims, No Drawings

OTHER PUBLICATIONS

Khetsuriani, et al., "Viral Meningitis-Associated Hospitalizations in the United States, 1988-1999," Neuroepidemiology, 2003, pp. 345-352, vol. 22.

Le Moullec, et al., "The Complete Sequence of Human Preprocalcitonin," FEBS Letter 1198, 1984, pp. 93-97, vol. 167, No. 1.

Maxson, et al., "Clinical Usefulness of Cerebrospinal Fluid Bacterial Antigen Studies," The Journal of Pediatrics, 1994, pp. 235-238, vol. 125.

Michelow, et al., "Value of Cerebrospinal Fluid Leukocyte Aggregation in Distinguishing the Causes of Meningitis in Children," The Pediatric Infectious Disease Journal, 2000, pp. 66-72, vol. 19.

Nigrovic, et al., "Development and Validation of a Multivariable Predictive Model to Distinguish Bacterial from Aseptic Meningitis in Chidren in the Post-Haemophilus Influenzae Era," Pediatrics, 2002, pp. 712-719, vol. 110.

Oostenbrink, et al., "Children with Meningeal Signs," Archives of Pediatrics & Adolescent Medicine, 2002, pp. 1189-1194, vol. 156.

El Bashir, et al., "Diagnosis and Treatment of Bacterial Meningitis," Archives of Disease in Childhood, 2003, pp. 615-620, vol. 88.

Sáez-Llorens, et al., "Bacterial Meningitis in Neonates and Children," Infectious Disease Clinics of North America, 1990, pp. 623-644, vol. 4, No. 4.

Tatara, et al., "Serum C-Reactive Protein in the Differential Diagnosis of Childhood Meningitis," Pediatrics International, 2000, pp. 541-546, vol. 42.

Tunkel, et al., "Practice Guidelines for the Management of Bacterial Meningitis," Clinical Infectious Diseases, 2004, pp. 1267-1284, vol. 39.

Schwarz, et al., "Serum Procalcitonin Levels in Bacterial and Abacterial Meningitis," Critical Care Medicine, 2000, pp. 1828-1832, vol. 28, No. 6.

Viallon, et al., "Diagnostic Rapide du Type de Méningite (Bactérienne ou Virale) par le Dosage de la Procalcitonine Sérique" La Presse Mèdicale, 2000, pp. 584-588, vol. 29, No. 11.

Gendrel, et al., "Procalcitonine, Protéine C-Rèactive et Interleukine 6 dans les Méningites Bactériennes et Virales de L'Enfant," La Presse Médicale, 1998, pp. 1135-1139, vol. 27, No. 23.

Taskin, et al., "Serum Procalcitonin and Cerebrospinal Fluid Cytokines Level in Children with Meningitis," Mediators of Inflammation, 2004, pp. 269-273, vol. 13, No. 4.

Gendrel, et al., "Measurement of Procalcitonin Levels in Children with Bacterial or Viral Meningitis," Clinical Infectious Diseases, 1997, pp. 1240-1242, vol. 24.

Viallon, et al., "Decrease in Serum Procalcitonin Levels Over Time During Treatment of Acute Bacterial Meningitis," Critical Care, 2005, pp. R344-R350.

Hatherill, et al., "Diagnostic Markers of Infection: Comparison of Procalcitonin with C Reactive Protein and Leucocyte Count," Archives of Diseases in Childhood, 1999, pp. 417-421, vol. 81.

Seehusen, et al., "Cerebrospinal Fluid Analysis," American Family Physician, 2003, pp. 1103-1108, vol. 68, No. 6.

Donald, et al., "Cerebrospinal Fluid C-Reactive Protein in Infective Meningitis in Childhood," Journal of Laboratory and Clinical Medicine, 1985, pp. 424-427, vol. 106, No. 4.

Author Unknown, "Total Protein (Micro) Assay," Diagnostic Chemicals Limited, 2002, pp. 1-4.

Author Unknown, "BRAHMS PCT—Instruction Manual," 2005, 6 pp., BRAHMS Aktiengesellschaft, Hennigsdorf, Germany.

Wikkelsö, et al., "Isoelectric Focusing Followed by Silver Staining. A Suitable Method for Routine Investigation of Cerebrospinal Fluid Proteins," European Neurology, pp. 306-312, 1984, vol. 23, No. 4. (Abstract only).

Krause, et al., "Normalbereich des Gesamteiweisses und der Eiweissfraktionen des Liquor Cerebrospinalis bei Kindern," Zeitschrift für Klinische Chemie und Klinische Biochemie, 1975, pp. 137-142, vol. 13, No. 4.

Siegert, et al., "Agarose Gel Electrophoresis of Cerebrospinal Fluid Proteins and Analysis of the Pherogram Profiles by Analog Computer," Journal of Clinical Chemistry & Clinical Biochemistry, 1977, pp. 635-644, vol. 15.

Jerrard, et al., "Clinical Laboratory in Emergency Medicine: Cerebrospinal Fluid," The Journal of Emergency Medicine, 2001, pp. 171-178, vol. 21, No. 2.

Adam, et al., "Cerebrospinal Fluid: Laboratory Reference for CSF and Neuroimmunology Homolka Hospital, Prague, Czech Republic," Advances in Clinical Chemistry, 2001, pp. 1-62, vol. 36.

* cited by examiner

DISTINCTION BETWEEN BACTERIAL MENINGITIS AND VIRAL MENINGITIS

CROSS-REFERENCE TO RELATED APPLICATIONS

The present application is a National Phase of and claims the benefit of PCT/FR2006/002734, with an International Filing Date of Dec. 14, 2006, which in turn claims priority to French Patent Application No. 05/12687, filed Dec. 14, 2005, the entire disclosures of which are incorporated by reference herein.

The present invention relates to the field of the distinction between bacterial meningitis and viral meningitis. It relates in particular to a method for detecting an infection of bacterial meningitis type, mainly including determining biological parameters such as the concentration of procalcitonin in blood and the concentration of proteins present in cerebrospinal fluid.

Acute meningitis is a common infection, mostly of viral origin (82-94%) and can therefore resolve spontaneously. However, when it is of bacterial origin (6-18%), meningitis can be fatal and is frequently associated with severe neurological after-effects, particularly when diagnosis and treatment begin at a late stage. Currently, due to the difficulty in quickly and accurately distinguishing between bacterial meningitis and viral meningitis, patients who are diagnosed with meningitis are treated rapidly with antibiotics and hospitalized, and their treatment continues until the origin of the meningitis has been clearly diagnosed. The consequences of this systematic administration of antibiotics to patients who have been diagnosed with meningitis are considerable not only on the economic plane, but also in medical terms. Indeed, this type of administration contributes to the risk of developing bacterial strains with resistance to antibiotics, the incidence of nosocomial infections and, above all, has a high cost. A study conducted in the USA has therefore shown that hospitalizing patients infected with viral meningitis represented an annual cost of 250 to 300 million dollars (Khetsuriani et al. *Neuroepidemiology* 2003, vol. 22, pages 345-352).

Therefore, it seems necessary to establish a quick and easy diagnosis that makes it possible to distinguish between bacterial meningitis and viral meningitis, with a sensitivity of 100% for bacterial meningitis.

Numerous clinical signs are known for distinguishing between bacterial meningitis and viral meningitis with a certain sensitivity as described in the articles by Michelow et al. (*Pediatr. Infect. Dis. Journal*, 2000, vol. 19, pages 6-72) and Tatara et al. (*Pediatr. Int.*, 2000, vol. 42, pages 541-546). Examples of these clinical signs include purpura, the appearance called "septic and/or toxic" and convulsions, which can contribute to a diagnosis of bacterial meningitis. However, these clinical signs are not always present and detectable in patents infected with bacterial meningitis.

Bacteriological tests also exist which can yield results with high levels of specificity, but these tests do not reach the required sensitivity of 100% for bacterial meningitis. There is therefore still a risk with such tests that they will not identify all the patients infected with bacterial meningitis. Such tests cannot therefore be used to prevent the systematic administration of antibiotics to patients who have been diagnosed with meningitis. Examples of bacteriological tests include Gram staining or studies of bacterial antigens in the cerebrospinal fluid, as described in the publications by Nigrovic et al. (*Pediatrics*, 2002, vol. 110, pages 712-719), Saez-Llorens et al. (*Lancet*, 2003, vol. 88, pages 615-620), Tunkel et al. (*Clin. Infect. Dis.*, 2004, vol. 39, pages 1267-1284), Maxson et al. (*J. Pediatr.*, 1994, vol. 125, pages 235-238). Biological markers have also been suggested for improving etiological diagnosis of meningitis, as described in the publications by Saez-Llorens et al. (*Lancet,* 2003, vol. 88, pages 615-620) and Tunkel at al. (*Clin. Infect. Dis.,* 2004, vol. 39, pages 1267-1284). Examples of the biological markers suggested include markers present in blood, such as C-reactive protein, leucocytes including neutrophilic leucocytes, markers present in cerebrospinal fluid such as proteins, glucose, leucocytes including neutrophilic leucocytes and markers present in blood and cerebrospinal fluid such as procalcitonin as described in Ferriere et al. (*Annales de Biologie Clinique,* 2000, vol. 58, pages 46-59), Jereb et al. (*Infection,* 2001, vol. 29, pages 209-212), Mary et al. (*Annales de Biologie Clinique,* 2003, vol. 61, pages 127-137), Bender et al. (*Neurology, vol.* 63, pages 1311-1313), Gendrel et al. (*Med. Mal. Infect.,* vol. 26, pages 1068-1072).

Numerous rules combining these clinical signs and/or biological markers have been suggested for the purpose of distinguishing between bacterial meningitis and viral meningitis.

An example is the rule by Jaeger et al. (*Eur. J. Clin. Microbiol. Infect. Dis.* 200, vol. 19, pages 1418-1421) which is a model based on determining the concentration of glucose and leucocytes in blood and the concentration of neutrophilic leucocytes and proteins in cerebrospinal fluid.

The rule by Bonsu et al. (*Pediatr. Infect. Dis. J.,* 2004, vol. 23, pages 511-517) is a fractional polynomial equation based on determining the concentration of neutrophilic leucocytes and proteins in cerebrospinal fluid, also taking the age of the patient into account.

The rule by Freedman et al. (*Arch. Pediatr. Adolesc. Med.,* 2001, vol. 155, pages 1301-1306) is based on a list of different characteristics including patient age, cerebrospinal fluid Gram stain and concentration of leucocytes, proteins and glucose in cerebrospinal fluid.

The rule by Nigrovic et al. (*Pediatrics,* 2002, vol. 110, pages 712-719) is also based on a list of characteristics including presence of convulsions in the patient, concentration of neutrophilic leucocytes in blood, cerebrospinal fluid Gram stain, concentration of neutrophilic leucocytes and proteins in cerebrospinal fluid.

The rule by Ooestenbrink et al. (*Arch. Pediatr. Adolesc. Med.,* 2002, vol. 156, pages 1189-1194) associates clinical elements with biochemical elements in a complex grid.

However, as of today, no quick and straightforward test exists for distinguishing between bacterial meningitis and viral meningitis with the required sensitivity of 100% for bacterial meningitis and with sufficiently high specificity.

The inventors have defined a quick and straightforward method for early detection of the presence of bacterial meningitis with a sensitivity of 100% for bacterial meningitis and a specificity of more than 50%.

Thus, a first aim of the invention relates to an in vitro method for detecting the presence of bacterial meningitis, comprising:
  i) determining the concentration of procalcitonin present in a test blood sample; and
  ii) comparing the concentration thus determined to the concentration of procalcitonin present in a reference sample or to a reference value.

Bacterial meningitis is understood to be an inflammation of the meninges which may be caused by various types of germs, mainly three: meningococcus (*Neisseria meningitidis*), pneumococcus (*Streptococcus pneumoniae*) and *Haemophilus influenzae* type b.

Procalcitonin is understood to be the protein precursor of calcitonin, with 116 single-stranded amino acids, described by Le Molluec J M et al. (SEQ ID NO: 8 of U.S. Pat. No. 6,905,687, FEBS Letter, 1984, pages 167-193), commonly referred to as ProCT or PCT. Although it can be found in various tissues, procalcitonin is mostly synthesized in the liver. Experiments conducted on animals and humans lead to believe that procalcitonin is involved in the inflammatory reaction, although this role has not yet been clearly established.

Test blood sample is understood to be a blood sample from an individual likely to be infected with bacterial meningitis. Blood samples can be obtained using techniques that are well known to those skilled in the art, for example with a needle equipped with a syringe inserted in a vein of the forearm or antecubital fossa of an individual. A sample of 1 to 3 ml of blood obtained from a child may be sufficient to implement the method according to the present invention. The blood sample can advantageously be treated so as to inhibit the normal bactericidal properties of blood and any possible antimicrobial agents by diluting the blood and adding inhibitors such as sodium polyetholsulfonate (SPS) with a concentration of 0.025%.

The test blood sample advantageously corresponds to a sample of serum or plasma from an individual whose status needs to be determined with regard to bacterial meningitis. Such a sample of serum or plasma can be easily obtained by those skilled in the art, by blood sample centrifugation and supernatant recovery.

The reference sample in step ii) is understood to be any sample in which the concentration of procalcitonin after comparing it to the concentration of procalcitonin in said test blood sample shows the presence of bacterial meningitis in said individual from whom the test blood sample was taken.

In fact, the inventors have proven that individuals infected with bacterial meningitis have a high concentration of procalcitonin in blood compared to healthy individuals or those infected with viral meningitis. Thus, the inventors have been able to determine that a concentration of procalcitonin higher than or equal to 0.5 ng/ml in the test blood sample provides the conclusion that the tested individual is infected with bacterial meningitis. A concentration of procalcitonin of 0.5 ng/ml can therefore be given as a reference value.

Examples of the reference sample in step ii) include blood samples taken from healthy individuals or individuals infected with viral meningitis, blood serum samples taken from healthy individuals or individuals infected with viral meningitis, blood plasma samples taken from healthy individuals or individuals infected with viral meningitis or even a solution of procalcitonin with a given concentration.

Healthy individual is understood to mean an individual who is free from pathologies.

Viral meningitis is understood to be an inflammation of the meninges which can be caused by various viruses such as enteroviruses, including Echovirus, Coxsackie and, more rarely, viruses of the herpes group, such as herpes 1 and 2, Cytomegalovirus, Epstein-Barr virus, varicella-zona viruses, HHV6 virus and, more rarely, arboviroses.

According to one preferred embodiment of said method according to the invention, said reference sample from step ii) is a solution of procalcitonin with a given concentration.

Solution of procalcitonin with a given concentration is understood to mean a solution of procalcitonin with a concentration comprised between 0.05 ng/ml and 10 ng/ml, preferably between 0.1 ng/ml and 1 ng/ml and preferentially of 0.5 ng/ml. Such a solution can be easily obtained by those skilled in the art, by diluting a given amount of purified and/or recombinant procalcitonin in a volume of water or a buffer solution, such as PBS. Such a purified and/or recombinant protein can be obtained in particular using the techniques described in U.S. Pat. No. 6,905,687.

The determination of the concentration of procalcitonin present in a test blood sample can be carried out according to techniques that are well known to those skilled in the art. Examples of such techniques include quantitative immunological techniques using antibodies or antibody fragments that specifically bind procalcitonin, such as the ELISA technique or also the techniques described in Patent Application PCT WO 97/20213.

According to a second preferred embodiment of the method according to the invention, the determination of the concentration of procalcitonin present in a test blood sample includes placing the sample in contact with an antibody that specifically binds procalcitonin.

The determination of the concentration of procalcitonin with the help of an antibody that specifically binds procalcitonin can be carried out using techniques that are well known to those skilled in the art such as, for example, quantitative immunological techniques such as the ELISA technique, the techniques described in Patent Application PCT WO 97/20213, the technique described by Giuliani et al. (*Cancer Res.*, 1989, vol. 49, pages 6845-6851) and the methods implemented in the LUMItest® kits, also known as B.R.A.H.M.S. PCT LIA, B.R.A.H.M.S. PCT KRYPTOR® and LIAISON B.R.A.H.M.S. PCT available from B.R.A.H.M.S. Diagnostica (Berlin, Germany). Said quantitative immunological techniques can use monoclonal antibodies which specifically bind procalcitonin marked directly or indirectly using a second antibody marked, for example, by an enzyme such as peroxidase, alkaline phosphatase or β-galactosidase, by a luminescent reagent such as fluorescein, rhodamine or cyanine or with the help of a second biotinylated antibody.

The antibodies or antibodies fragments that specifically bind procalcitonin can be polyclonal or monoclonal antibodies. The antibodies fragments that specifically bind procalcitonin can be chosen from among the group comprising fragments Fab, F(ab')2, FV and sFv. Examples of monoclonal antibodies that specifically bind procalcitonin include the antibodies described in U.S. Pat. No. 6,451,311, U.S. Pat. No. 5,330,909 and U.S. Pat. No. 6,133,427, the antibodies available from ABCAM with references "ab14813", ab11498", "ab11494", "ab14817", "ab14816", "ab24454", the antibodies available from CHEMICON with reference "MAB3490" and the antibodies available from GeneTex®, Inc. with references "GTX14813", GTX11498", "GTX11494", "GTX14817" and "GTX14816".

According to a third preferred embodiment of said method according to the invention, said method can also comprise:
iii) determining the concentration of proteins present in a test cerebrospinal fluid sample; and
iv) comparing the concentration thus determined to the concentration of proteins in a reference sample or to a reference value.

Cerebrospinal fluid proteins are understood to be the proteins present in the fluid contained in the spaces delimited by the meninges and the ventricles of the brain. Examples of cerebrospinal fluid proteins include prealbumin, albumin, α1-globulin, α2-globulin, β1-globulin, β2-globulin and γ-globulin.

Test cerebrospinal fluid sample is understood to be a cerebrospinal fluid sample from an individual likely to be infected with bacterial meningitis. In the method according to the invention, the test blood sample and the test cerebrospinal fluid sample are taken from the same individual. The cerebrospinal fluid samples can be obtained using techniques that are well known to those skilled in the art, for example lumbar puncture.

The reference sample in step iv) is understood to be any sample in which the concentration of proteins after comparing it to the concentration of proteins in said test cerebrospinal fluid sample shows the presence of bacterial meningitis in said individual from whom the test cerebrospinal fluid sample was taken.

In fact, the inventors have proven that individuals infected with bacterial meningitis have a high concentration of proteins in their cerebrospinal fluid compared to healthy individuals or those infected with viral meningitis. Thus, the inventors have been able to determine that a concentration of proteins in cerebrospinal fluid higher than or equal to 0.5 g/l in the test cerebrospinal fluid sample provides the conclusion that the tested individual is infected with bacterial meningitis. An example of a reference value is therefore a concentration of proteins in cerebrospinal fluid of 0.5 g/l.

The method according to the invention, by identifying individuals whose concentration of procalcitonin is higher than or equal to 0.5 ng/ml and/or whose concentration of proteins in cerebrospinal fluid is higher than or equal to 0.5 g/l, allows the identification of individuals infected with bacterial meningitis with a sensitivity of 100%.

Examples of the reference sample in step iv) include cerebrospinal fluid samples taken from a healthy individual or taken from an individual infected with viral meningitis or a solution of proteins with a given concentration.

According to a fourth preferred embodiment of said method according to the invention, said reference sample from step iv) can correspond to a solution of proteins with a given concentration.

Solution of proteins with a given concentration is understood to mean a solution of proteins with a concentration comprised between 0.05 and 5 g/l, preferably between 0.1 and 1 g/l and, in a particularly preferred manner, 0.5 g/l. Such a solution can be easily obtained by those skilled in the art, by diluting a given amount of proteins, in particular BSA (Bovine Serum Albumin) with the desired concentration in a volume of water or a buffer solution such as PBS (Phosphate Buffered Saline).

The determination of the concentration of proteins present in a test cerebrospinal fluid sample can be carried out according to techniques that are well known to those skilled in the art, such as immunological techniques using antibodies or antibodies fragments that specifically bind cerebrospinal fluid proteins, techniques based on measuring the enzymatic activity of said cerebrospinal fluid proteins, molecular biology tests, physical tests, chemical tests such as calorimetric tests, determining the mass of said cerebrospinal fluid proteins by mass spectroscopy.

According to a fifth preferred embodiment of said method according to the invention, step iii) of determining the concentration of proteins in cerebrospinal fluid is carried out by means of a calorimetric test.

A calorimetric test includes placing said cerebrospinal fluid sample in contact with a calorimetric reagent which reacts with said proteins and makes it possible to determine the concentration thereof. Examples of calorimetric tests include colouring methods using acetic methanol, amidoblack or pyrogallol red used for example in the kit available from ROCHE DIAGNOSTICS with reference "03515826".

Advantageously, said individual from whom such test blood sample and possibly said test cerebrospinal fluid sample are taken is aged from 2 weeks to 25 years, preferably from 3 weeks to 18 years, and most preferably from 1 month to 16 years.

Also advantageously, the method according to the invention is carried out on test samples taken from an individual who has been certified to be infected with meningitis, which is therefore potentially bacterial in origin.

Examples of such individuals include individuals having more than 5 leucocytes/mm$^3$, preferably more than 7 leucocytes/mm$^3$ in their cerebrospinal fluid as described in the publications by Greenlee et al. (*Dis. Clin. North. Am.,* 1990, vol. 4, pages 583-598) and Saez-Llorens et al. (*Dis. Clin. North Am.,* 1990, vol. 4, pages 623-644). The determination of the concentration of leucocytes present in cerebrospinal fluid can be carried out using techniques well known to those skilled in the art.

Also advantageously, the method according to the invention is not performed on test blood samples and possibly on test cerebrospinal fluid samples taken from individuals whose likelihood of being infected with bacterial meningitis is such that the implementation of said method according to the invention is pointless.

Examples of such individuals include individuals who have previously undergone brain surgery, individuals with depressed immune systems and/or individuals having purpura, septic and/or toxic appearance and/or convulsions.

A depressed immune system is understood to mean a reduction or suppression of the immune reactions of a body.

Purpura is understood to refer to haemorrhagic spots caused by blood spilled from skin or mucosa capillaries, which can result in petechiae or ecchymoses. These spots are bright red or bluish in colour and do not disappear with pressure.

Septic and/or toxic appearance is understood to mean when an individual has a lethargic appearance, signs of poor perfusion such as pale skin colour, ashen skin as described in the publication by Baker et al. (*Pediatrics,* 1990, vol. 85, pages 1040-1043) signs of hypoventilation or hyperventilation or cyanosis such as described in the publication by Baraff et al. (*Pediatrics,* 1993, vol. 2, pages 1-12).

Convulsions are understood to refer to involuntary and instant contractions determining movements localized in one or several muscle groups or generalized throughout the entire body.

Also advantageously, the method according to the invention is not carried out on samples whose quality does not allow the method according to the invention to be implemented.

Examples of such samples include cerebrospinal fluid samples which, when taken, cause localized hemorrhaging in the patient. Such cerebrospinal fluid samples therefore have an erythrocyte concentration of more than 12,000 erythrocytes/mm$^3$, preferably more than 10,000 erythrocytes/mm$^3$. The determination of the concentration of erythrocytes present in the cerebrospinal fluid sample can be carried out using techniques well known to those skilled in the art.

Also advantageously, the method according to the invention is not implemented on test samples taken from patients who received antibiotic treatment in the 48 hours preceding the taking of said test blood samples and possibly test cerebrospinal fluid samples.

Antibiotic treatment is understood to mean the administration of an antibiotic chosen from the group comprising the β-lactamin family such as penicillin and ampicillin, cephalosporins, the aminoglycoside family such as gentamicin, the phenicol family such as chloramphenicol.

The method according to the invention can also include complementary steps for identifying the presence of bacteria in said test samples.

Such identification steps are well known to those skilled in the art. Examples of such steps include Gram staining of the test cerebrospinal fluid sample. Gram staining of the test cerebrospinal fluid sample can be carried out using techniques that are well known to those skilled in the art, such as Gram's method modified by Hucker. Gram staining is a differential staining method based on the greater permeability of the walls of Gram-negative bacteria in alcohol. It consists, initially, of creating an alcohol-soluble staining complex (crystal violet—Lugol's iodine) which stains the cytoplasm of all the bacterial purple. A second step involves decolorizing with alcohol, which can easily cross the wall of Gram-negative bacteria, and which dissolves the staining complex. In Gram-positive bacteria, the wall cannot be crossed. Gram staining of the cerebrospinal fluid allows the detection of meningitis-causing bacteria such as *H. influenzae, S. pneumoniae, N. meningitides, H. influenzae* and *N. meningitidis* are Gram-negative bacteria, while *S. pneumoniae* is a Gram-positive bacteria.

A second aim of the invention relates to a method for diagnosing the presence of bacterial meningitis in an individual including, in addition to implementing one of the previously described in vitro methods, a first step of taking a blood sample from said individual and, possibly, a cerebrospinal fluid sample from said individual.

Blood and cerebrospinal fluid samples can be easily obtained using previously described sampling techniques.

According to one preferred embodiment of the method according to the invention, it also includes a step of administering antibiotics to patients in whom the presence of bacterial meningitis has been diagnosed.

A third aim of the invention relates to a kit comprising:
means for detecting procalcitonin.

The kit according to the invention makes it possible to diagnose the presence of bacterial meningitis in an individual.

Means for detecting procalcitonin are understood to refer to means for implementing quantitative immunological techniques comprising antibodies or antibodies fragments which specifically bind the procalcitonin protein. Such detection means make it possible to determine the concentration of procalcitonin in a blood sample.

According to one preferred embodiment of the kit according to the invention, said means for detecting procalcitonin are antibodies or antibodies fragments which specifically bind procalcitonin.

Antibodies is understood to refer to polyclonal or monoclonal antibodies, preferably monoclonal antibodies.

Examples of monoclonal antibodies that specifically bind procalcitonin include the antibodies described in U.S. Pat. No. 6,451,311, U.S. Pat. No. 5,330,909 and U.S. Pat. No. 6,133,427, the antibodies available from ABCAM with references "ab14813", "ab11498", "ab11494", "ab14817", "ab14816", "ab24454", the antibody available from CHEMICON with reference "MAB3490" and the antibodies available from GeneTex®, Inc. with references "GTX14813", GTX11498", "GTX11494", "GTX14817" and "GTX14816".

Antibodies fragments which specifically bind procalcitonin are understood to be fragments Fab, F(ab')2, FV and sFv of monoclonal antibodies which specifically bind procalcitonin.

The kit according to the invention advantageously also includes a procalcitonin solution with a given concentration as a reference sample.

Solution of procalcitonin with a given concentration is understood to mean a solution of procalcitonin with a concentration comprised between 0.05 ng/ml and 10 ng/ml, preferably between 0.1 ng/ml and 1 ng/ml and preferentially of 0.5 ng/ml.

According to a second preferred embodiment of the kit according to the invention, said kit also comprises means allowing the detection of proteins, preferably in a cerebrospinal fluid sample.

Means allowing the detection of proteins in a cerebrospinal fluid sample is understood to refer to any means that can reveal the presence of proteins in a cerebrospinal fluid sample such as antibodies directed against cerebrospinal fluid proteins, enzymes making it possible to reveal the activity of said proteins, or reagents which react with said proteins making it possible to determine their concentration, such as stains. Such means make it possible to determine the concentration of proteins in a cerebrospinal fluid sample.

Advantageously, said means allowing the detection of proteins in a cerebrospinal fluid sample are calorimetric reagents which react with said proteins and make it possible to determine the concentration of proteins in said sample. Examples of such calorimetric reagents include pyrogallol red, solutions of amidoblack, solutions of acetic methanol or a combination of the above.

Also advantageously, the kit according to the invention also comprises a solution of proteins with a given concentration.

Solution of proteins with a given concentration is understood to mean a solution of proteins with a concentration comprised between 0.05 and 5 g/l, preferably between 0.1 and 1 g/l and, in a particularly preferred manner, 0.5 g/l.

According to a third preferred embodiment of the kit according to the invention, said kit also comprises a list of instructions to be followed in order to use said detection means to diagnose the presence of bacterial meningitis in an individual.

A fourth aim of the invention corresponds to the use of a kit as previously described to manufacture a tool for diagnosing bacterial meningitis.

According to one preferred embodiment of the use according to the invention, said diagnosis tool is intended for individuals aged from 2 weeks to 25 years, preferably from 3 weeks to 18 years, and most preferably from 1 month to 16 years.

According to a second preferred embodiment of the use according to the invention, said diagnosis tool is intended for individuals who have been certified to be infected with meningitis, which is therefore potentially bacterial in origin.

Examples of such individuals include individuals from whom a cerebrospinal fluid sample contains more than 5 leucocytes/mm$^3$, preferably more than 7 leucocytes/mm$^3$.

According to a third preferred embodiment of the use according to the invention, said diagnosis tool is not intended for individuals whose likelihood of being infected with bacterial meningitis is such that the implementation of said diagnosis tool is pointless.

Examples of such individuals include individuals who have previously undergone brain surgery, individuals with depressed immune systems and/or individuals having purpura, a septic and/or toxic appearance and/or convulsions.

According to a fourth preferred embodiment of the use according to the invention, said diagnosis tool is not intended for individuals having received antibiotic treatment in the 48 hours preceding the taking of a blood sample and, possibly, a cerebrospinal fluid sample from said individuals.

According to a fifth preferred embodiment of the use according to the invention, said diagnosis tool is not intended for individuals having more than 12,000 erythrocytes/mm$^3$, preferably more than 10,000 erythrocytes/mm$^3$, in their cerebrospinal fluid.

A fifth aim of the invention corresponds to the use of a kit according to the invention in a method for detecting the presence of bacterial meningitis.

A sixth aim of the invention corresponds to a method for identifying the presence of bacterial meningitis comprising a step a) of comparing the concentration of procalcitonin present in a test blood sample taken from an individual to the concentration of procalcitonin present in a reference sample or to a reference value.

According to one preferred embodiment of the method for identifying the presence of bacterial meningitis according to the invention, said method can also comprise a step b) of comparing the concentration of proteins present in a test cerebrospinal fluid sample taken from an individual to the concentration of proteins present in a reference sample or to a reference value.

Advantageously, said comparison or comparisons are carried out by computerized means, preferably by a computer.

These comparisons make it possible to issue a diagnosis regarding bacterial meningitis for said individual.

Also advantageously, the method according to the invention can include printing out a report.

According to another preferred embodiment of the method for identifying the presence of bacterial meningitis according to the invention, the method is implemented on an individual aged from 2 weeks to 25 years, preferably from 3 weeks to 18 years, and most preferably from 1 month to 16 years.

According to another preferred embodiment of the method for identifying the presence of bacterial meningitis according to the invention, the method is implemented on an individual whose cerebrospinal fluid contains more than 5 leucocytes/mm$^3$, preferably more than 7 leucocytes/mm$^3$.

According to yet another preferred embodiment of the method for identifying the presence of bacterial meningitis according to the invention, the method is not implemented on an individual whose likelihood of being infected with bacterial meningitis is such that the implementation of said method is pointless.

Examples of such individuals include individuals who have previously undergone brain surgery, individuals with depressed immune systems and/or individuals having purpura, a septic and/or toxic appearance and/or convulsions.

According to yet another preferred embodiment of the method for identifying the presence of bacterial meningitis according to the invention, the method is not implemented on individuals having received antibiotic treatment in the 48 hours preceding the taking of a blood sample and, possibly, a cerebrospinal fluid sample.

According to yet another preferred embodiment of the method for identifying the presence of bacterial meningitis according to the invention, the method is not implemented with concentrations of procalcitonin and, possibly, of proteins in cerebrospinal fluid obtained from samples of insufficient quality.

Examples of such samples include cerebrospinal fluid samples which, when taken, caused localized hemorrhaging in the patient. Such cerebrospinal fluid samples therefore have an erythrocyte concentration of more than 12,000 erythrocytes/mm$^3$, preferably more than 10,000 erythrocytes/mm$^3$.

The following examples are provided in a non-limiting fashion merely for the purpose of illustrating the invention.

EXAMPLES

I. Example 1

Detection of the Presence of Bacterial Meningitis in a Population of 201 Patients, 21 of Whom are Infected with Bacterial Meningitis I.1 Population Studied The study was based on 201 children admitted to Saint-Vincent de Paul Hospital in Paris between 2000 and 2004 for patients infected with viral meningitis and between 1995 and 2004 for patients infected with bacterial meningitis. The interest of this study lies mainly in the fact that it was conducted on a large population of patients in whom the presence of meningitis was clearly established at a later stage, after the vaccination campaign against *Haemophilus influenzae* b, which started in 1994 as described in the publication by Dumonceaux et al. (*Archives de Pediatrie*, 1999, vol. 6, pages 617-624).

The application to these 201 patients of different known rules to differentiate bacterial meningitis and viral meningitis as described above (rules by Jaeger et al., Bonsu et al., Freedman et al., Ooestenbrink et al.) did not provide a quick and straightforward identification of the patients infected with bacterial meningitis with a sensitivity of 100%, good specificity and good clinical applicability. Only the rule by Nigrovic et al. made it possible to detect all the patients infected with bacterial meningitis with good specificity and good clinical applicability. However, the application of this rule by Nigrovic et al. to a large population of 890 patients showed that this rule does not have a sensitivity of 100% for bacterial meningitis.

As regards the prior art, the Inventors have therefore sought to define a quick and easy method for differentiating between bacterial meningitis and viral meningitis with a sensitivity of 100% for bacterial meningitis.

Among these 201 children, only patients aged from 28 days to 16 years were taken into consideration for the study to test the efficiency of the method for detecting the presence of bacterial meningitis according to the invention.

In addition, among these 201 patients, only patients having more than 7 leucocytes/mm$^3$ in their cerebrospinal fluid were taken into consideration for the study.

Among these 201 patients, individuals whose likelihood of being infected with bacterial meningitis was such that the implementation of the method according to the invention was pointless were not taken into consideration for this study. Thus, patients who had undergone brain surgery, individuals with depressed immune systems and/or individuals having purpura, a septic and/or toxic appearance and/or convulsions were excluded from this study.

In addition, among these 201 patients, the individuals from whom the quality of their samples did not allow the implementation of the method according to the invention were not taken into consideration in this study. Thus, patients in whom the taking of a cerebrospinal fluid sample resulted in hemorrhaging, when these patients had more than 10,000 erythrocytes/mm.sup.3, were excluded from this study.

Likewise, patients having received antibiotic treatment in the 48 hours preceding the taking of test blood samples and possibly cerebrospinal fluid were excluded from this study.

Therefore, of these 201 patients, only 167 were used to test the efficiency of the method for detecting the presence of bacterial meningitis according to the invention.

Among these 167 patients on whom the study was conducted, 146 patients were diagnosed with viral meningitis and 21 patients were diagnosed with bacterial meningitis. Among these 21 patients, 11 were admitted to Saint-Vincent de Paul Hospital in Paris between 1995 and 1999 and 10 between 2000 and 2004. The pathogens responsible for the bacterial meningitis in these 21 patients were *Streptococcus pneumoniae* in 10 patients, *Neisseria meningitidis* in 9 patients, *Haemophilus influenza* b in 1 patient and *Streptococcus* group B in 1 patient.

I.2 Determining the Concentration of Procalcitonin in a Test Blood Sample Taken from a Patient 3 ml of blood were taken from each one of the 167 patients using a needle equipped with a syringe inserted into a vein of the antecubital fossa of the patients.

The blood samples were centrifuged for 10 minutes at 3,800 rpm at room temperature (around 20° C.) and the plasma was then recovered using a plastic pipette.

The concentration of procalcitonin in these samples was determined using an immunoluminometric technique by means of the LUMItest® PCT kit available from BRAHMS Diagnostica according to the procalcitonin dosage instructions supplied with the kit.

I.3 Determining the Concentration of Proteins in a Test Cerebrospinal Fluid Sample Taken from a Patient 2 ml of cerebrospinal fluid were taken from each of the 167 patients by means of a lumbar puncture. The samples were then quickly used for the dosage of total proteins by means of the calorimetric method using pyrogallol red with the kit available from Roche Diagnostics with reference "03515826" and according to the instructions supplied with the kit.

I.4 Determining the Presence of Bacterial Meningitis

The presence of bacterial meningitis in a patient was then determined according to the concentration of procalcitonin in the patient's blood and the concentration of proteins in the patient's cerebrospinal fluid; these concentrations were obtained using the methods respectively described in the preceding paragraphs I.1 and I.2. The number of patients having a concentration of procalcitonin in their blood greater than or equal to 0.5 ng/ml (PCT≧0.5 ng/ml) and/or a concentration of proteins in their cerebrospinal fluid greater than or equal to 0.5 g/l (CSF≧0.5 g/l) was determined.

|  | Bacterial meningitis (n-21) | | Viral meningitis (n = 146) | |
| --- | --- | --- | --- | --- |
|  | n | % | n | % |
| PCT ≧ 0.5 ng/ml | 16 | 89 | 15 | 11 |
| PCT < 0.5 ng/ml | 2 | 11 | 119 | 89 |
| CSF ≧ 0.5 g/l | 18 | 86 | 31 | 22 |
| CSF < 0.5 g/l | 3 | 14 | 112 | 78 |
| PCT ≧ 0.5 ng/ml or CSF ≧ 0.5 g/l | 21 | 100 | 85 | 58 |

The inventors have therefore shown that all the patients infected with bacterial meningitis either had a concentration of procalcitonin in their blood greater than or equal to 0.5 ng/ml (PCT≧0.5 ng/ml) or a concentration of proteins in their cerebrospinal fluid greater than or equal to 0.5 g/l (CSF≧0.5 g/l).

In addition, the inventors have proven that by determining a concentration of procalcitonin in a patient's blood greater than or equal to 0.5 ng/ml or a concentration of proteins in a patient's cerebrospinal fluid greater than or equal to 0.5 g/l makes it possible to detect all the patients infected with bacterial meningitis.

Indeed, the two patients with bacterial meningitis who have a concentration of procalcitonin in their blood of less than 0.5 ng/ml have a concentration of proteins in their cerebrospinal fluid greater than or equal to 0.5 g/l. The three patients with bacterial meningitis having a concentration of proteins in their cerebrospinal fluid of less than 0.5 g/l have a concentration of procalcitonin in their blood greater than 0.5 ng/l.

Therefore, the Inventors have proven that the combination of the two biological parameters—concentration of procalcitonin in an individual's blood and concentration of protein in an individual's cerebrospinal fluid—makes it possible quickly and easily to detect the presence of bacterial meningitis in a patient with a sensitivity of 100%.

II. Example 2

Detection of the Presence of Bacterial Meningitis in a Population of 202 Patients of Whom 87 are Infected with Bacterial Meningitis The efficiency of the method for detecting the presence of bacterial meningitis according to the invention was tested on a population of 202 patients of whom 87 patients were infected with bacterial meningitis. The study was carried out as described previously in example 1. The method according to the invention made it possible to detect all the patients infected with bacterial meningitis.

The invention claimed is:

1. An in vitro method for detecting the presence of bacterial meningitis comprising:
   i) determining the concentration of procalcitonin present in a test blood sample; and
   ii) determining the concentration of proteins present in a test cerebrospinal fluid sample,
   wherein the concentration of procalcitonin in the test blood sample of greater than or equal to 0.5 ng/ml and the concentration of proteins in the cerebrospinal fluid of greater than or equal to 0.5 g/l indicates the presence of bacterial meningitis.

2. A method according to claim 1, wherein step i) is carried out using quantitative immunological techniques.

3. A method according to claim 1, wherein the step ii) is carried out by a colorimetric test.

4. A method according to claim 1, wherein said test blood sample and said test cerebrospinal fluid sample come from an individual aged from 2 weeks to 25 years.

5. A method according to claim 1, wherein said test blood sample and said test cerebrospinal fluid sample are taken from an individual who has been certified to be infected with meningitis.

6. A method according to claim 1, wherein said test blood sample and said test cerebrospinal fluid sample are not taken from an individual having previously undergone neurosurgery, an individual with a depressed immune system and/or an individual having purpura, a septic and/or toxic appearance and/or convulsions.

7. A method according to claim 1, wherein said test blood sample and said test cerebrospinal fluid sample are not taken from an individual having received antibiotic treatment in the 48 hours preceding the taking of said test blood sample and said test cerebrospinal fluid sample.

8. A method according to claim 1, wherein said test cerebrospinal fluid sample does not have an erythrocyte concentration of more than 12,000 erythrocytes/mm$^3$.

9. A method according to claim 1, further comprising the step of Gram staining the test cerebrospinal fluid sample.

10. A method according to claim 1, wherein said test cerebrospinal fluid sample does not have an erythrocyte concentration of more than 10,000 erythrocyte s/mm$^3$.

11. A method according to claim 5, wherein said individual has more than 5 leucocytes/mm$^3$ in his/her cerebrospinal fluid.

12. A method according to claim 5, wherein said individual has more than 7 leucocytes/mm$^3$ in his/her cerebrospinal fluid.

13. A method according to claim 1, wherein said test blood sample said test cerebrospinal fluid sample come from an individual aged from 3 weeks to 18 years.

* * * * *